US005352591A

United States Patent [19]
Wong et al.

[11] Patent Number: 5,352,591
[45] Date of Patent: Oct. 4, 1994

[54] ALDOLASE ENZYME PROCESS FOR MAKING 5-AZIDO-5-DEOXY-HEXULOSE-1-PHOSPHATE

[75] Inventors: Chi-Huey Wong, Rancho Santa Fe; Kun-Chin Liu, San Diego, both of Calif.

[73] Assignee: The Scripps Research Institute, La Jolla, Calif.

[21] Appl. No.: 93,782

[22] Filed: Jul. 19, 1993

Related U.S. Application Data

[60] Division of Ser. No. 835,238, Feb. 13, 1992, Pat. No. 5,229,523, which is a continuation-in-part of Ser. No. 707,594, May 30, 1991, abandoned.

[51] Int. Cl.$^5$ .................. C12P 17/10; C12P 19/02; C07D 207/30
[52] U.S. Cl. .................. 435/121; 548/541; 435/105
[58] Field of Search .................. 548/541; 435/121

[56] References Cited

PUBLICATIONS

*Enzyme Nomenclature 1992*, Academic Press, Inc., San Diego (1992), pp. 459–464.

*Primary Examiner*—David B. Springer
*Attorney, Agent, or Firm*—Welsh & Katz, Ltd.

[57] ABSTRACT

2-Methyl-5-hydroxymethyl-and 2,5-dimethyl-3,4-dihydroxypyrrolidines, their processes of preparation and use are disclosed. 5-Azido-5-deoxy-hexulose-1-phosphate compounds and processes of making the same are also disclosed.

6 Claims, No Drawings

ALDOLASE ENZYME PROCESS FOR MAKING 5-AZIDO-5-DEOXY-HEXULOSE-1-PHOSPHATE

This invention was made with government support under Contract No. GM 44154 awarded by the National Institutes of Health. The government has certain rights in the invention.

CROSS-REFERENCE TO RELATED APPLICATION

This application is a division of application Ser. No. 07/835,238, filed Feb. 13, 1992, now U.S. Pat. No. 5,229,523, which is a continuation-in-part of co-pending application Ser. No. 07/707,594 filed May 30, 1991, now abandoned, whose disclosures are incorporated by reference.

TECHNICAL FIELD

The present invention relates to disubstituted dihydroxypyrrolidines or disubstituted-azafuranoses, and more particularly to 2-methyl-5-hydroxymethyl- and 2,5-dimethyl-3,4-dihydroxypyrrolidines, their preparation and uses.

BACKGROUND OF THE INVENTION

Carbohydrates are a large class of natural substances that structurally are polyhydroxycarbonyl compounds and their derivatives. Carbohydrates generally correspond to the formula $(C)_n(H_2O)_n$, where n is an integer usually greater than 3.

Monosaccharides are simple carbohydrates that cannot be further hydrolyzed into simpler types of carbohydrate. A monosaccharide having a five-membered ring is referred to as a furanose. A furanose lacking one or more hydroxyl groups normally present in a carbohydrate is referred to as deoxy-furanose, with the carbon chain position at which the hydroxy is absent being indicated.

Azasugars are a class of saccharides in which the ring oxygen is replaced by an imino group (—NH—). A five-membered ring azasugar can be referred to as an azafuranose or a polyhydroxylated pyrrolidine compound, as well as being named as an aza derivative of an otherwise systematically or trivially named furanose monosaccharide.

As used herein, azasugars derived from pyrrolidines (azafuranoses) are hydroxylated at the 3 and 4 positions, have a hydroxymethyl group at the 5-position, and a methyl or hydroxymethyl at the 2-position, the 1 position being the nitrogen atom, in pyrrolidine nomenclature. A 2-hydroxymethyl group in pyrrolidine nomenclature corresponds to a 4-hydroxymethyl or 5-hydroxyl group in furanose nomenclature. Pyrrolidine nomenclature and numbering will usually be used herein, unless otherwise specified.

Azasugars and their derivatives have been identified as potent glycosidase inhibitors [Paulsen et al., *Adv. Carbohydr. Chem.* 1968, 23, 115; Fellows, *Chem. Br.* 1987, 23, 842; Truscheit et al., *Angew. Chem. Int. Ed. Engl.* 1981, 20, 744; Inouye et al., *Tetrahedron* 1968, 24, 2125; Muller, in *Biotechnology*, Rehm, H.-J. et al., eds., VCH Verlagsgesellschaft Weinheim 1985, Vol. 4, Chapter 18]. As such, azasugars can be useful for treating metabolic disorders such as diabetes [Liu, *J. Org. Chem.* 1987, 52, 4717; Bayer et al., Ger. Offen. DE 3620645; Anzeveno et al., *J. Org. Chem.* 1989, 54, 2539; Yoshikuni et al., *J. Pharmacobio-Dyn* 1988, 111, 356] or as antiviral agents [Karpas et al., *Proc. Natl. Acad. Sci.* 1988, .85, 9229; Walker et al., *Proc Natl. Acad. Sci.* 1987, 84, 8120; Winkler et al., *J. Med. Chem.* 1989, 32, 2084], as antimicrobial [Evans et al. *J. Phytochemistry* 1985, 24, 1953] and as anticancer agents [Humphries, M. J., et al. *Cancer Res.* 1986, 46, 5215].

Despite their clear usefulness, there is still a need for an effective synthesis of novel azasugars and their derivatives [Fleet, *Chem, Br.* 1989, 25, 287 and references cited therein; Bernotas et al., *Tetrahedron Lett.* 1985, 26, 1123; Setoi et al. *Chem. Pharm. Bull.* 1986, 34, 2642; Legler et al., *Carbohydr.. Res,* 1984, 128, 61; Kinast et al., *Angew. Chem. Int. Ed. Engl.* 1981, 20, 805; Hanesian, *Chem. Ind.* 2966, 2126; Schmidt et al., *Justus Liebigs Ann. Chem.* 2989, 5, 423; Pederson et al., *Tetrahedron Lett,* 1988, 29, 4645; Ziegler et al., *Angew. Chem. Int. Ed. Engl.* 1988, 29, 716; Buchanan et al., *J. Chem. Soc. Perkin Trans.* 1990, 699; Fleet et al., *J. Chem. Soc. Perkin Trans.* 1989, 665; Dondoni et al., *J. Chem. Soc. Chem. Commun.* 1990, 854; Fleet et al., *Chem. Lett.* 1986, 1051; Chen et al., *Tetrahedron Lett.* 1990, 31, 2229; Ciufolini et al., *J. Am. Chem. Soc.* 1989, 111, 3473].

Naturally occurring azasugars include 1-deoxynojirimycin (1,5-dideoxy-1,5-imino-D-glucitol), 1-deoxymannojirimycin (1,5-dideoxy-1,5-imino-D-mannitol), and castanospermine (1,6,7,8tetrahydroxyoctahydroindolizine). 1-Deoxynojirimycin was isolated from plants of the genus Morus [Yagi et al., *Nippon Nogei Kagaku Kaishi* 1976, 50, 5751; Vasella et al., *Helv. Chim. Acta.* 1982, 65, 1134] and from strains of Bacillus [Daigo et al., *Chem. Pharm. Bull.* 1986, 34, 2243]. 1-Deoxymannojirimycin was isolated from the legume Lonchocarpus [Fellows et al., *J. C. S. Chem. Comm.* 1979, 977]. Castanospermine is a plant alkaloid isolated from seeds of an Australian chestnut tree, *Castanospermum australe* [Saul et al. *Arch. Biochem. Biophys.* 1983, 221, 593]. Isolation of azasugars from nature is often expensive and time consuming. Therefore, several methods have been developed for the synthesis of these important compounds.

Both synthetic and semi-synthetic routes have been used in these syntheses [Inouye et al., *Tetrahedron* 1968, 24, 2125; Paulsen et al., *Chem. Ber.* 1967, 100, 802; Saeki et al., *Chem. Pharm. Bull.* 1968, 16, 2477; Paulsen et al., *Adv. Carbohydr. Chem.* 1968, 23, 115; Kinast et al., *Angew. Chem. Int. Ed. Engl.* 1981, 20, 805; Bernotas et al., *Tetrahedron Lett,* 1984, 25, 165; Bernotas, *Tetrahedron Lett.* 1985, 26, 1123; Setoi et al., *Chem. Pharm. Bull.* 1986, 34, 2642; Iida, *J. Org. Chem.* 1987, 52, 3337]. Natural sugars have been used as starting materials, but multiple protection and deprotection steps are required. For example, glucose was used in the synthesis of 1-deoxynojirimycin and 1-deoxymannojirimycin [Fleet, *Chem. Br.* 1989, 25, 287 and references cited therein; Bernotas et al., *Tetrahedron Lett.* 1985, 26, 1123; Chen et al., *Tetrahedron Lett.* 1990, 31, 2229].

An enzymatic synthesis based on fructose-1,6-diphosphate (FDP) aldolase (EC 4.1.2.3) has been recently developed and has proven to be a powerful approach for the synthesis of some azasugars [Pederson et al., *Tetrahedron Lett.* 1988, 29, 4645; von der Osten et al., *J. Am. Chem. Soc.* 1989, 111, 3924; Pederson et al., *Heterocycles* 1989, 28, 477; Ziegler et al., *Angew. Chem. Int. Ed. Engl.* 1988, 29., 716; Straub et al., *J. Org. Chem.* 1990, 55, 3926]. This enzymatic method involves the use of FDP aldolase from either rabbit muscle or *Escherichia coli* to catalyze the aldol condensation of dihydroxyacetone phosphate (DHAP; a donor substrate) with any of a number of possible omega-azidoaldehydes as a second, acceptor substrate [Durrwachter et al., *J. Am. Chem. Soc.* 1986, 108, 7812; Durrwachter et al. *J. Org. Chem.* 1988, 53, 4175; Pederson et al., *Tetrahedron Lett.* 1988, 29, 4645; Bednarski et al. *Tetrahedron Lett.* 1986, 27, 5807]. The omega-azidoketose phosphate produced is dephosphorylated and then reductively cyclized to form a deoxynojirimycin compound.

For instance, if DHAP is reacted with (RS)-3-azido-2-hydroxypropanal in the presence of FDP aldolase, the 2-epimers 1-deoxynojirimycin and 1-deoxymannojirimycin are produced upon catalytic reductive amination of the dephosphorylated enzyme reaction products [Pederson, R. L., et al. *Tetrahedron Lett.* 1988, 29, 4645].

After synthesis, 1-deoxynojirimycin can then be easily converted into castanospermine [Hamana et al., *J. Org. Chem.* 1987, 52, 5494]. The latter compound has been shown to inhibit the processing of the AIDS virus gp160 envelope protein precursor, and to modify the envelope glycoprotein, thus affecting the ability of the virus to enter cells [Walker et al., *Proc. Natl. Acad. Sci.* 1987, 84, 8120].

The synthesis of hydroxylated piperidines and pyrrolidines from dicarbonyl sugars via a one-step double reductive amination reaction has recently been reported. Reitz et al., *Tetrahedron Lett.*, 1990, 31(47):6777. According to such a synthetic scheme, 2,5-anhydro-imino-D-glucitol and 1-deoxynojirimycin were prepared by reacting 5-keto-D-fructose and 5-keto-D-glucose, respectively, with benzhydrylamine in the presence of a borohydride reducing agent (NaCNBH$_3$, MeOH).

Of the pyrrolidine-type azasugars reported, (2R,5R)-dihydroxymethyl-(3R,4R)-dihydroxypyrrolidine (Compound X, hereinafter) [Welter et al, *Phytochemistry*, 1976, 25, 747; Fleet et al., *Tetrahedron Lett.*, 1985, 26, 1469; Shing, *J. Chem. Soc. Chem. Commun.*, 1987, 262; Dureault et al., *Synlett*, 1991, 4, 225] showed a broad spectrum of inhibition against glycosidases, including α- and β-glucosidases and β-xylosidase [Fleet et al., *Tetrahedron Lett.* 1985, 26, 3127]. As there is no apparent structural similarity between that reported apparent structural similarity between that reported 2,5-disubstituted pyrrolidine and hexoses that are the natural enzyme substrates, the inhibition may be due to a different mode of binding.

It would therefore be of interest if one could examine the inhibition properties of diastereomers of Compound X and other derivatives. It would also be beneficial if the range of glycosidase enzymes inhibited by Compound X diastereomers and derivatives thereof could be broadened still further to include still other glycosidases. The disclosure that follows discusses such compounds.

BRIEF SUMMARY OF THE INVENTION

In one aspect, the present invention contemplates a 2,5-dimethyl- or 2-methyl-5-hydroxymethyl-3,4-dihydroxypyrrolidine, their processes of manufacture and use, as well as intermediates in their preparation. A compound of the invention has the formula I, below:

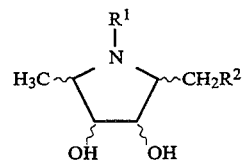

wherein
R$^1$ is selected from the group consisting of hydrogen, C$_1$–C$_{12}$ alkyl, C$_7$–C$_{10}$ aralkyl and C$_1$–C$_{12}$ acyl, or >N—R$^1$ is a C$_1$–C$_{12}$ alkyl or C$_7$–C$_{10}$ aralkyl N-oxide; and
R$^2$ is hydrogen or hydroxyl.

In one embodiment, the present invention contemplates 2-methyl-5-hydroxymethyl- 3,4-dihydroxypyrrolidines (formula I where R$^2$ is hydroxyl), their processes of manufacture and use, as well as intermediates in their preparation. Such a compound corresponds in structure to formula Ia, below:

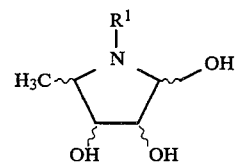

wherein
R$^1$ is as defined above for formula I.

In a preferred embodiment, the 5-hydroxymethyl group has the 5S configuration, the 3-hydroxy and 4-hydroxy groups have the 3R,4R configuration, and the compound structure corresponds to formula II, below:

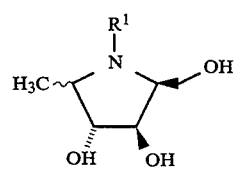

wherein
R$^1$ is as defined above.
Preferably, R$^1$ is hydrogen and the 2-methyl group has the 2R configuration.

In another aspect, the present invention contemplates a process of making a 5-azido-5-deoxy-hexulose-1-phosphate comprising mixing a 2-azido-substituted-propionaldehyde and dihydroxyacetone phosphate in the presence of a catalytic amount of an aldolase to form a reaction mixture and maintaining the reaction mixture under biological reaction conditions for a time period sufficient to form the 5-azido-5-deoxy-hexulose-1-phosphate.

In a preferred embodiment, the 2-azido-substituted-propionaldehyde is 2-azido-3-hydroxypropanal and the formed compound is 5-azido-5-deoxyhexulose-1-phosphate.

In another preferred embodiment, the 2-azido-substituted propionaldehyde is 2-azidopropanal and the formed compound is 5-azido-5,6-dideoxy-hexulose-1-phosphate.

The aldolase used in that process is preferably selected from the group consisting of FDP aldolase, Rham-1-P-aldolase, Fuc-1-P-aldolase and TDP aldolase. In a preferred embodiment, the aldolase is FDP aldolase, the 2-azido-substituted-propionaldehyde is 2-azido-3-hydroxy-propanal and the formed compound is 5-azido-5-deoxy-L-xylo-hexulose-1-phosphate.

A composition of one of the before-described compounds in an aqueous medium is also contemplated. The dihydroxypyrrolidine compound is present in the composition in a glycosidase-inhibiting amount.

DETAILED DESCRIPTION OF THE INVENTION

The Compounds

A compound of the invention is generally referred to herein as a substituted pyrrolidine, a substituted-3,4-dihyroxypyrrolidine or more generally as an azafuranose. Particular compounds are named specifically as derivatives of pyrrolidine.

A compound of the invention has structural formula I, below:

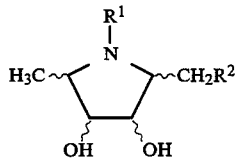

wherein
$R^1$ is selected from the group consisting of hydrogen, $C_1$–$C_{12}$ alkyl, $C_7$–$C_{10}$ aralkyl and $C_1$–$C_{12}$ acyl, or $>N$—$R^1$ is a $C_1$–$C_{12}$ alkyl or $C_7$–$C_{10}$ aralkyl N-oxide; and
$R^2$ is hydrogen or hydroxyl.

As used herein, straight or wavy lines between the ring and the substituent groups are meant to imply that substituents can be in the α- or β-configuration. Darkened wedge-shaped lines indicate that a substituent is in a β-configuration, extending upwardly from the plane of the ring, whereas dashed wedge-shaped lines indicate a substituent in the α-configuration, extending downwardly from the plane of the ring.

In the above formula I, and in the other formulae and compounds disclosed herein, only one group at each of the ring carbon atoms is shown. The fourth, unshown group bonded to each of those ring carbons is a hydrogen atom, as would be present in an unsubstituted carbohydrate. By way of example, in the above structural formula I, the methyl depicted at the pyrrolidine 2-position indicates in actuality that there is one methyl and one hydrogen at that position.

Turning to the $R^1$ group, it is first to be noted that a $C_1$–$C_{12}$ alkyl group is also present in a $C_1$–$C_{12}$ alkyl N-oxide group, so those alkyl groups will be discussed only once. Contemplated $C_1$–$C_{12}$ alkyl groups include methyl, ethyl, propyl, iso-propyl, n-butyl, sec-butyl, iso-butyl, t-butyl, pentyl, hexyl, heptyl, octyl, iso-octyl, nonyl, decyl, undecyl and dodecyl. A $C_1$–$C_{12}$ acyl group is the corresponding acyl group to $C_1$–$C_{12}$ alkyl groups, with the understanding that iso-propyl, sec- and t-butyl and similarly structured alkyl groups have no corresponding acyl groups. A contemplated $C_7$–$C_{10}$ aralkyl group includes benzyl, phenethyl, (p-ethyl)-phenethyl, and the like.

An $>N$—$R^1$ group is a $C_1$–$C_{12}$ alkyl or a $C_7$–$C_{10}$ aralkyl N-oxide. Here, the alkyl group is as discussed above, and the alkylated tertiary nitrogen atom is oxidized to form the N-oxide. The symbol ">" is used to show the remaining valences of the nitrogen that are bonded to ring carbon atoms.

As initially synthesized using the process discussed hereinafter, $R^1$ is hydrogen. Hydrogen is thus a preferred $R^1$ group. That preference relates to all of the compounds herein.

In one embodiment, $R^2$ is hydroxyl and the present invention contemplates a 2-methyl-5-hydroxymethyl-pyrrolidine. A preferred compound according that embodiment has formula Ia, below:

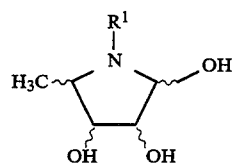

wherein
$R^1$ is as defined above for formula I.

Certain configurations of the substituent groups are preferred. In one preferred embodiment, the hydroxyl groups at the pyrrolidine 3- and 4-positions are both in the R configuration and the hydroxymethyl group at the pyrrolidine 5-position is in the S configuration. A compound of that configuration has the structural formula II, below:

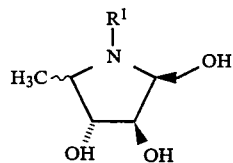

where
$R_1$ is as defined above for formula I.

Turning to specific compounds, two compounds (Compounds 1 and 101), of formula II are particularly preferred. Of those, Compound 101 is most preferred. The structural formulae of Compounds 1 and 101 are shown below.

Compound 1 can be named (2R)-methyl-(5S)-hydroxymethyl-(3R,4R)-dihydroxypyrrolidine. Compound 101 can be named (2S)-methyl-(5S)-dihydroxymethyl-(3R,4R)-dihydroxypyrrolidine.

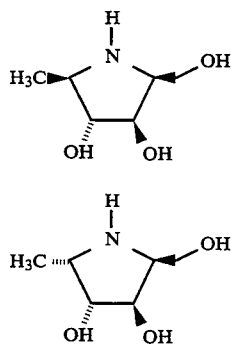

As can be seen from the above structures, Compound 1 and Compound 101 are identical except for the configuration of the 2-position methyl group.

A mixture of Compounds 1 and 101 was found to be a potent inhibitor of glycosidase, and in particular fucosidase, activity (See Example 10 hereinafter).

Yet another embodiment of this invention relates to compounds in which R² is hydrogen. A compound in which R² is hydrogen is a 2,5-dimethyl- 3,4-dihydroxypyrrolidine, whose general structural formula is shown in formula Ib, below:

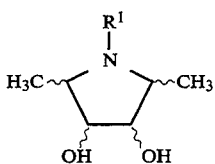

In another aspect, the present invention relates to a 2-hydroxymethyl-(5S)-hydroxymethyl-(3R,4R)-dihydroxypyrrolidine, which compound has formula III, below:

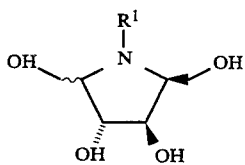

where
R¹ is as defined above for formula I.
In a preferred embodiment, R¹ is hydrogen, the hydroxymethly group at the pyrrolidine 2-position has the R configuration and the compound has the structure of Compound 2. The structural formulae of Compound 2 and previously known Compound X are shown below for purposes of comparison.

Compound 2 can be named (2R,5S)-dihydroxymethyl-(3R,4R)-dihydroxypyrrolidine. Compound X is named hereinbefore.

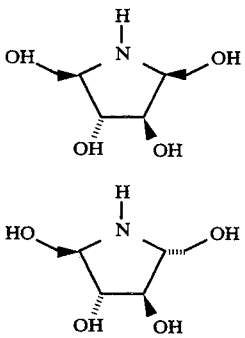

As can be seen from the above structures, Compound 2 of this invention and known Compound X are identical except for the configuration of the 5-position hydroxymethyl group. That seemingly small change in configuration is manifested in significant inhibition of an α-galactosidase and an α-mannosidase for Compound 2, where Compound X exhibited no inhibition. Inhibitions of an α- and a β-glucosidase by Compounds 2 and X were similar. Thus, unexpected glycosidase activity was found for Compound 2. (See Example 9 hereinafter).

Compound Preparation

Another aspect of the present invention relates to a process for the synthesis of some of the above dihydroxypyrrolidines. In accordance with that method, an azido-substituted ketose or an azido-substituted α-ketose phosphate compound having a six-carbon chain is reductively cyclized by hydrogenation in the presence of a palladium catalyst. The carbon atom of the azido substituent and the carbon atom of the keto group are separated in the chain by three carbon atoms, with the azido group being at other than an omega-position on the chain.

In accordance with one process aspect, a 5-azido-5-deoxy-hexulose-1-phosphate is reductively cyclized by hydrogenation in the presence of a palladium catalyst such as palladium on charcoal (Pd—C) to form a 2-methyl-5-hydroxymethyl-dihydroxypyrrolidine. By way of example, 5-azido-5-deoxy-L-xylo-hexulose-1-phosphate is reductively cyclized by hydrogenation in the presence of a palladium catalyst such as palladium on charcoal (Pd—C) to form Compound I and its diastereomer Compound 101.

In another process aspect, a 5-azido-5-deoxyhexulose is reductively cyclized by hydrogenation in the presence of a palladium catalyst to form a 2,5-dihydroxymethyl-3,4-dihydroxypyrrolidine. By way of example, 5-azido-5-deoxy-L-xylo-hexulose-1-phosphate is reductively cyclized by hydrogenation in the presence of a palladium catalyst such as palladium on charcoal (Pd—C) to form Compound 2 and its diastereomer, Compound 102.

In accordance with another method aspect, a 5-azido-5,6-dideoxy-hexulose-1-phosphate is reductively cyclized by hydrogenation in the presence of a palladium catalyst such as palladium on charcoal (Pd—C) to form a 2,5-dimethyl-3,4-dihydroxypyrrolidine. By way of example, 5-azido-5,6-dideoxy-L-xylo-hexulose-1-phosphate is reductively cyclized by hydrogenation in the presence of a palladium catalyst such as palladium on charcoal (Pd—C) to form Compound Ia and its diastereomer Compound 101a.

In another process aspect, a 5-azido-5,6-dideoxy-hexulose, as can be formed by phosphatase cleavage of a corresponding 1-phosphate compound, is reductively cyclized by hydrogenation in the presence of a palladium catalyst to form a 2,5-dihydroxymethyl-3,4-dihydroxypyrrolidine. By way of example, 5-azido-5,6-dideoxy-L-xylo-hexulose-1-phosphate is reductively cyclized by hydrogenation in the presence of a palladium catalyst such as palladium on charcoal (Pd—C) to form Compound 2a and its diastereomer, Compound 102a.

An azido-substituted α-ketose phosphate compound used to form a dihydroxypyrrolidine can be prepared in a number of standard chemical manners, as is apparent from its relatively simple structure. Such standard preparations tend, however, to provide the desired azido-substituted α-ketose phosphate compound in relatively low yields of mixtures. Those mixtures can be separated prior to reductive cyclization-hydrogenolysis by usually used chromatographic techniques.

It is preferred, however, to use enzymatic syntheses to form the desired azido-substituted α-ketose phosphate compounds. Enzymes that are particularly useful for such syntheses are the aldolases. According to such an enzymatic synthetic method, a phosphorylated donor ketone (e.g. dihydroxyacetone phosphate, DHAP) is mixed with an azido-substituted-propionaldehyde (e.g. 2-azido-3-hydroxypropanal or 2-azidopropanal) in the presence of a catalytic amount of an aldolase enzyme to form a reaction mixture. The reaction mixture is then maintained under biological reaction conditions for a period of time sufficient to form the desired azido-substituted α-ketose phosphate compound.

Where the azido-aldehyde is 2azido-3-hydroxypropanal, and the donor ketone is DHAP, the formed azido-substituted α-ketose phosphate compound is a 5-azido-5-deoxy-hexulose-1-phosphate. Where the azido-aldehyde is 2-azidopropanal, and the donor ketone is DHAP, the formed azido-substituted α-ketose phosphate compound is a 5-azido-5,6-dideoxy-hexulose-1-phosphate.

Biological reaction conditions are those that maintain the activity of the aldolase as well as the structural integrity of the formed azido-substituted α-ketose phosphate compound. Those conditions include a temperature range of about 0° C. to about 45° C., a pH value range of about 5 to about 9 and an ionic strength varying from that of distilled water to that of about one molar sodium chloride. Methods for optimizing such conditions are well known in the art.

The synthesis of dihydroxypyrrolidines according to such a synthetic process is shown generally without stereoconfiguration in Scheme 1, below, wherein $R^2$ is as defined above for formula I.

of the cyclic imine intermediate to which the hydrogen is added. Schemes 2-5 and 2a-5a, hereinafter, illustrate each of the possible products from those reductive cyclizations.

In actual practice, it is found that a mixture of both possible cyclization products is obtained when hydrogenation is carried out without prior dephosphorylation. The isomer in which the methyl and adjacent ring hydroxyl groups are trans predominates in the mixture.

On the other hand, where the azido-substituted α-ketose phosphate compound is first dephosphorylated and then reductively cyclized, substantially only one of the two possible hydroxymethyl compounds is obtained. That obtained hydroxymethyl compound has a configuration in which the hydroxymethyl group, which formerly bore the phosphate, is trans to the adjacent hydroxyl group.

A. Reductive Cyclization by Hydrogenation

In carrying out the hydrogenation of the process of Scheme 1, substantially, any standard palladium catalyst can be used. Exemplary catalysts include palladium powder, palladium on activated carbon (Pd—C), palladium on alumina, palladium on barium sulfate and palla- Scheme 1

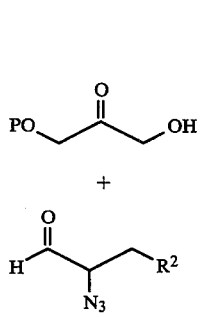
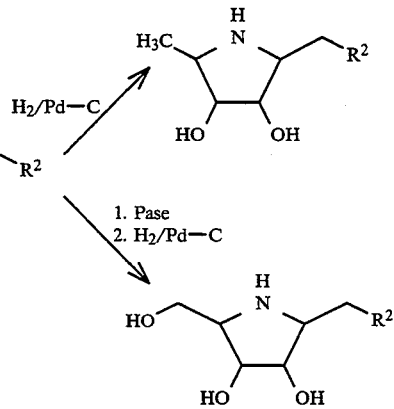

Following Scheme 1 to synthesize a methylhydroxymethyl-dihydroxypyrrolidine of formula Ia, the azido-substituted α-ketose phosphate compound where $R^2$ is hydroxyl is reductively cyclized by palladium-catalyzed hydrogenation ($H_2$/Pd—C) without dephosphorylation of the azido-substituted α-ketose phosphate compound. Where $R^2$ is hydrogen, a methylhydroxymethyl-dihydroxypyrrolidine is formed by dephosphorylation followed by palladium-catalyzed hydrogenation.

To form a dimethyl-dihydroxypyrrolidine of formula Ib, from an α-ketose phosphate whose $R^2$ group is hydrogen, that α-ketose phosphate is reductively cyclized by palladium-catalyzed hydrogenation, without prior dephosphorylation. The abbreviation PO is used in all of the schemes herein to mean a phosphate group.

To synthesize a dihydroxypyrrolidine of formula III, above, where the substituent group at the pyrrolidine 2-position is hydroxymethyl, the azido-substituted α-ketose phosphate compound is first dephosphorylated and then reductively cyclized by hydrogenation. The dephosphorylation is typically accomplished using a phosphatase enzyme (Pase) such as an acid phosphatase.

The reductive cyclization that is used in each of the generalized reactions shown in Scheme 1 can provide two stereoisomeric products, depending upon the side dium on calcium carbonate. Palladium on activated carbon (charcoal) is a preferred catalyst.

The hydrogenation is carried out at greater than atmospheric pressure such as at about 40–60 pounds per square inch (psi). A usual hydrogenation solvent such as water, ethanol or methanol, or mixtures thereof is also used.

A hydrogenation useful herein is thus seemingly similar to that used in the art to convert azido α-ketols to various nojirimycin derivatives. An important distinction exists however between those reactions and the hydrogenations described herein where the azido-substituted α-ketose phosphate is not dephosphorylated prior to reductive cyclization.

That distinction lies in the presence of a terminal (omega) phosphate group adjacent to (α to) the keto group of a reactant azido compound used herein. That phosphate group is lost during the reductive cyclization and is replaced by a hydrogen atom. Thus, a compound that is reductively cyclized without prior dephosphorylation is an azido α-ketose phosphate.

No precedent is known for this dephosphorylating hydrogenolysis reaction. Treatment of glucose 6-phosphate or dihydroxyacetone phosphate under the same conditions showed no reaction, thereby implicating the ring nitrogen atom in the hydrogenolysis reaction. Preliminary studies indicate that an imine phosphate derivative may be an intermediate in the loss of the phosphate group.

B. Aldolase Catalyzed Formation of Azido-substituted α-ketose Phosphate

The aldolase-catalyzed reaction of Scheme 1 is an aldol condensation. According to such a condensation reaction, a phosphorylated donor ketone (e.g. dihydroxyacetone phosphate, DHAP) is reacted with an azido-aldehyde (e.g. 2-azido-3-hydroxypropanal or 2-azidopropanal) in the presence of a catalytic amount of an aldolase enzyme. Of particular relevance to the present invention are fructose-1,6-diphosphate (FDP) aldolase (EC 4.1.2.3), rhamnulose-1-phosphate (Rham-1-P) aldolase (EC 4.1.2.19), fuculose-1-phosphate (Fuc-1-P) aldolase EC 4.1.2.17) and tagatose-1,6-diphosphate (TDP) aldolase.

Each of those enzymes can utilize dihydroxyacetone phosphate (DHAP) as a donor substrate and a number of aldehydes as acceptor substrates to form azido-substituted α-ketose phosphate compounds having new stereogenic centers with, for example, D-threo (3S,4R), L-threo (3R,4S), L-erythro (3R,4R), D-erythro (3S,4S), D-ribo (2R), D-glycero-D-allo (2R,3S) configurations.

An enzyme that is particularly useful for such syntheses is fructose-1,6-diphosphate (FDP) aldolase (EC 4.1.2.3), utilizes dihydroxyacetone phosphate (DHAP) as a donor substrate and an α-azido aldehyde as acceptor substrate. FDP aldolase is kinetically selective for the (R)-enantiomer. However, the kinetically formed aldol product is also unstable and the thermodynamic (S)-enantiomer product is also found to be formed. Thus, diastereomerically pure products are formed from a racemic aldehyde acceptor. No precedent is known for the use of an α-azido aldehyde as an acceptor substrate for FDP aldolase.

By selection of the aldolase enzyme and the use of a racemic azido aldehyde, one can control the isomeric configuration of the azido-substituted α-ketose phosphate compound and, thus, the stereochemistry of the cyclized azasugar. If formation of an azasugar with a desired configuration about a particular bond is not favored by the enzymatic aldol condensation leading to the azido α-ketose phosphate, that stereochemistry can be changed in the azido α-ketose phosphate or azasugar by selective blocking of hydroxyl or other reactive groups and inversion of the configuration of the desired substituent using well known organic chemical techniques.

Exemplary syntheses of precursor azido aldehydes, azido α-ketose phosphate and azasugars are discussed hereinafter.

It is to be pointed out that an azido-substituted α-ketose phosphate can exist in solution in a straight chain or cyclic, hemiacetal form. Upon reductive cleavage of the azido group in forming a primary amine that becomes the ring nitrogen atom of the azafuranose, the hemiacetal rearranges to form a cyclic imine that is further reduced to the azasugar.

An exemplary acceptor substrate for formation of a 2-methyl-5-hydroxymethyl-3,4-dihydroxypyrrolidine is 2-azido-3-hydroxypropanal. The azafuranose products prepared from each enzyme are diastereomers.

An exemplary acceptor substrate for formation of a 2,5-dimethyl-3,4-dihydroxypyrrolidine is 2-azidopropanal. The azafuranose products prepared from each enzyme are also diastereomers.

1. Fructose-1,6-diphosphate (FDP) Aldolase

As shown below in Scheme 2, 2-azido-3-hydroxypropanal is condensed with DHAP in the presence of FDP aldolase to form azido-substituted α-ketose phosphate Compound I. Compound I is then either (1) dephosphorylated (Pase) and then (2) reductively cyclized by hydrogenation ($H_2$/Pd—C), or directly reductively cyclized by hydrogenation ($H_2$/Pd—C).

Where Compound I is dephosphorylated prior to reductive cyclization by hydrogenation, two diastereomeric products, Compounds 2 and 102, are formed. Compounds 2 and 102 differ from each other only in the configuration of the hydroxymethyl group at the pyrrolidine 2-position.

In Compound 2, that pyrrolidine 2-position hydroxymethyl has the R configuration, extends upwardly from the plane of the ring, and is trans oriented relative to the hydroxyl group at the pyrrolidine 3-position. In diastereomer Compound 102, the pyrrolidine 2-position hydroxymethyl has the S configuration, extends downwardly form the plane of the ring, and is cis oriented relative to the hydroxyl group at the pyrrolidine 3-position.

Where Compound I is reductively cyclized by hydrogenation without prior dephosphorylation, diastereomeric products, Compounds I and 101, are formed. Compounds 1 and 101 differ from Compounds 2 and 102, respectively, in the nature of the substitutent group at the pyrrolidine 2-position. In an analogous manner to Compounds 2 and 102, Compounds 1 and 101, differ from each other in the configuration of the methyl group at the pyrrolidine 2-position.

In Compound 1, that pyrrolidine 2-position methyl has the R configuration, extends upwardly from the plane of the ring, and is trans oriented relative to the hydroxyl group at the pyrrolidine 3-position.

In diastereomer Compound 101, the pyrrolidine 2-position methyl has the S configuration, extends downwardly form the plane of the ring, and is cis oriented relative to the hydroxyl group at the pyrrolidine 3-position.

It can, thus, be seen that reductive cyclization by hydrogenation of an azido-substituted α-ketose phosphate compound, whether or not preceded by dephosphorylation, produces two diastereomeric products that differ only in the configuration and relative orientation of the pyrrolidine 2-position substitutent group. The diastereomer having an orientation trans to the pyrrolidine 3-position hydroxyl group is the predominant product.

The production of diastereomeric products from the reductive cyclization by hydrogenation of an azido-substituted α-ketose phosphate compound is independent of the steroconfiguration of that azido-substituted α-ketose phosphate compound. Thus, a large number of isomeric pyrrolidines can be made from DHAP and 2-azido-3-hyroxypropanal by combining various specific aldolase-catalyzed condensations with such reductive cyclization by hydrogenation. Exemplary syntheses of isomeric pyrrolidines using various aldolases are set forth below.

FDP-Aldolase can be obtained from commercial sources (Sigma Chemical Co., St. Louis, Mo.) or isolated from animal tissues such as rabbit muscle.

Scheme 2

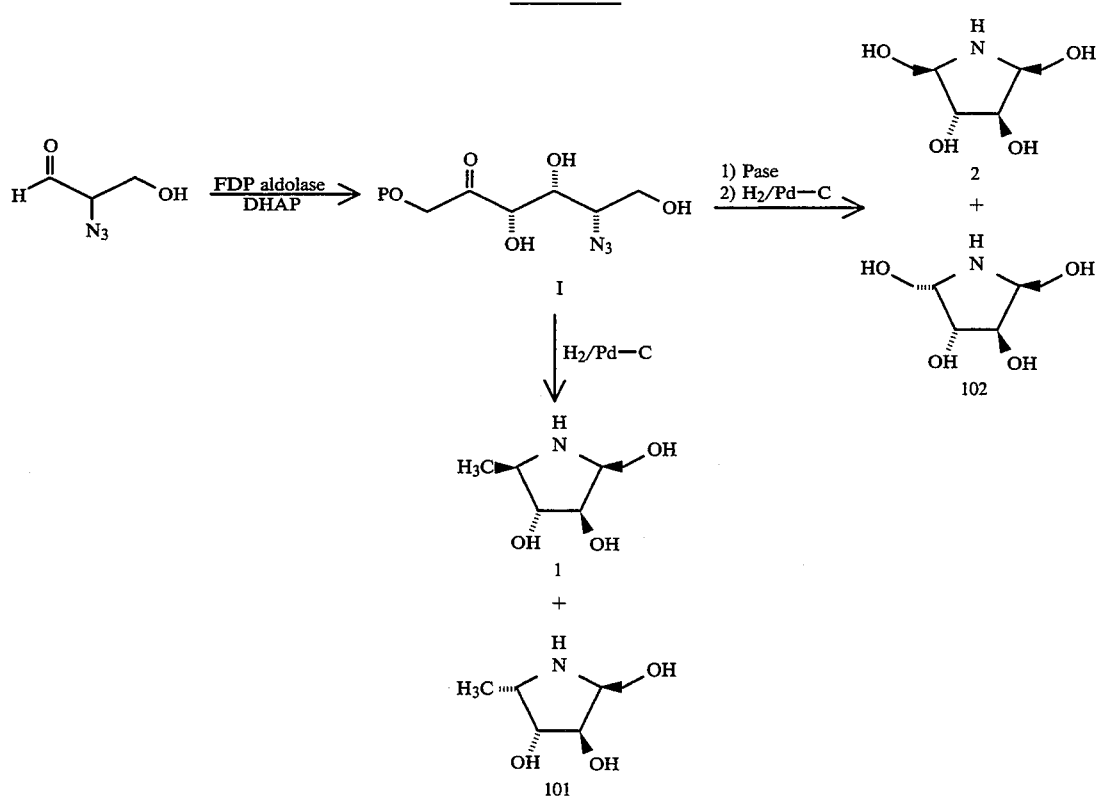

As shown below in Scheme 2a, 2-azidopropanal was condensed with DHAP in the presence of FDP aldolase to form azido-substituted α-ketose phosphate Compound Ia. Compound Ia was then either 1) dephosphorylated (Pase) and then 2) reductively cyclized by hydrogenation (H₂/Pd—C), or directly reductively cyclized by hydrogenation (H₂/Pd—C).

Where Compound Ia was dephosphorylated prior to reductive cyclization by hydrogenation, two diasteromeric products, compounds 2a and 102a, were formed.

Where Compound Ia was reductively cyclized by hydrogenation without prior dephosphorylation, diastereomeric products, Compounds 1a and 101a, were formed.

As used herein in Schemes 2a–5a, compounds designated with the letter "a" after a compound number have the same stereoconfiguration as the correspondingly numbered compound without the "a" suffix. By way of example, Compound 1a corresponds in stereoconfiguration to Compound 1. The only difference between Compound 1 and Compound 1a is the nature of the substituent group at the pyrrolidine 5-position. In Compound 1 and other numbered compounds, that substituent group is hydroxymethyl. In Compound 1a and other "a"-designated compounds, that substituent group is methyl.

Scheme 2a

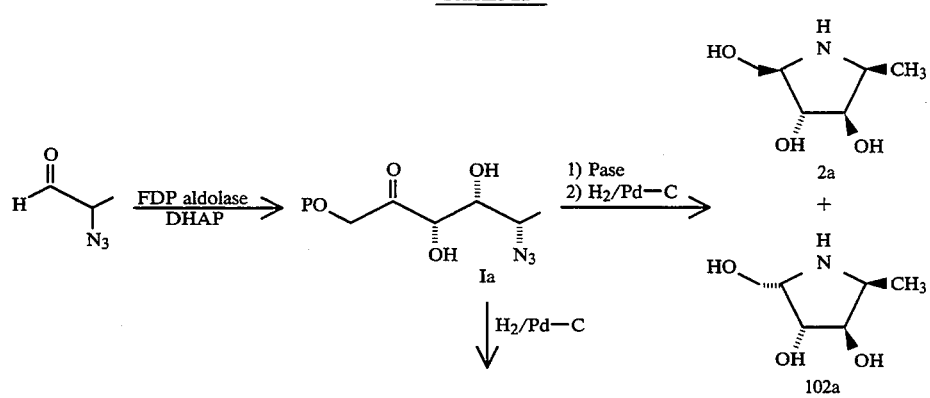

Scheme 2a

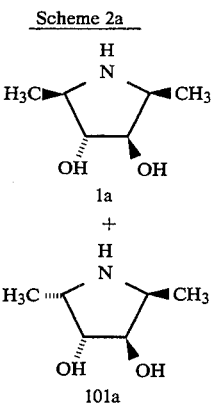

2. Rhamnulose-1-phosphate (Rham-1-p) Aldolase

As shown below in Scheme 3, where 2-azido-3-hydroxypropanal is condensed with DHAP in the presence of Rham-1-P aldolase, two azido-substituted α-ketose phosphate compounds are formed: a kinetic product (Compound II) and a thermodynamic product (Compound III). Where Compound II is 1) dephosphorylated and then 2) reductively cyclized by hydrogenation, diastereomeric compounds 103 and 104 are formed.

Where Compound III is directly reductively cyclized by hydrogenation, diastereomeric Compounds 105 and 106 are formed.

Where Compound III is 1) dephosphorylated and then 2) reductively cyclized by hydrogenation, diastereomeric Compounds 107 and 108 are formed.

Where Compound III is directly reductively cyclized by hydrogenation, diastereomeric Compounds 109 and 110 are formed.

Compounds 103, 104, 107 and 108 differ from Compounds 105, 106, 109 and 110, respectively, only in the nature of the substituent group at the pyrrolidine 2-position.

Compounds 103, 104, 105 and 106 differ from Compounds 2, 102, and 101, respectively, in the orientation of the substituent groups at the pyrrolidine 3- and 4-positions. In Compounds 2, 102, 1 and 101, those substituent groups have the 3R,4R configuration. In Compounds 103, 104, 105 and 106, those substituent groups have the 3S,4S configuration.

Compounds 107, 108, 109 and 110 differ from Compounds 102, 2, 101 and 1, respectively in the orientation of the substituent groups at the pyrrolidine 3-, 4- and 5-positions. In Compounds 102, 2, 101 and 1, those substituent groups have the 3R,4R, SS configuration. In Compounds 107, 108, 109 and 110, those substituent groups have the 3S,4S,5R configuration.

Rham-1-P Aldolase can be obtained from commercial sources (Sigma Chemical Co., St. Louis, Mo.) or isolated from *E. coli* strain K-40.

Scheme 3

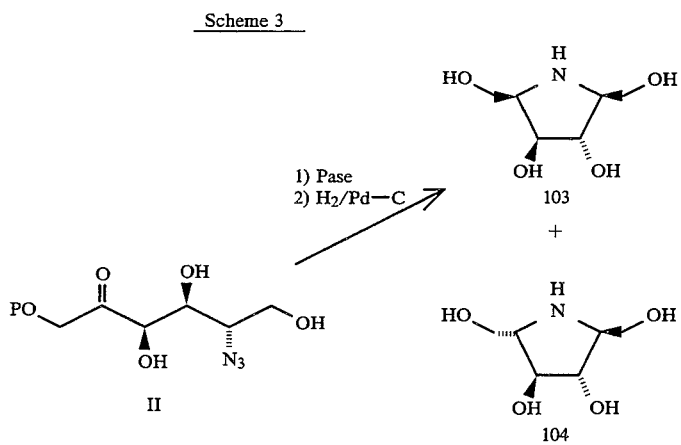

Scheme 3

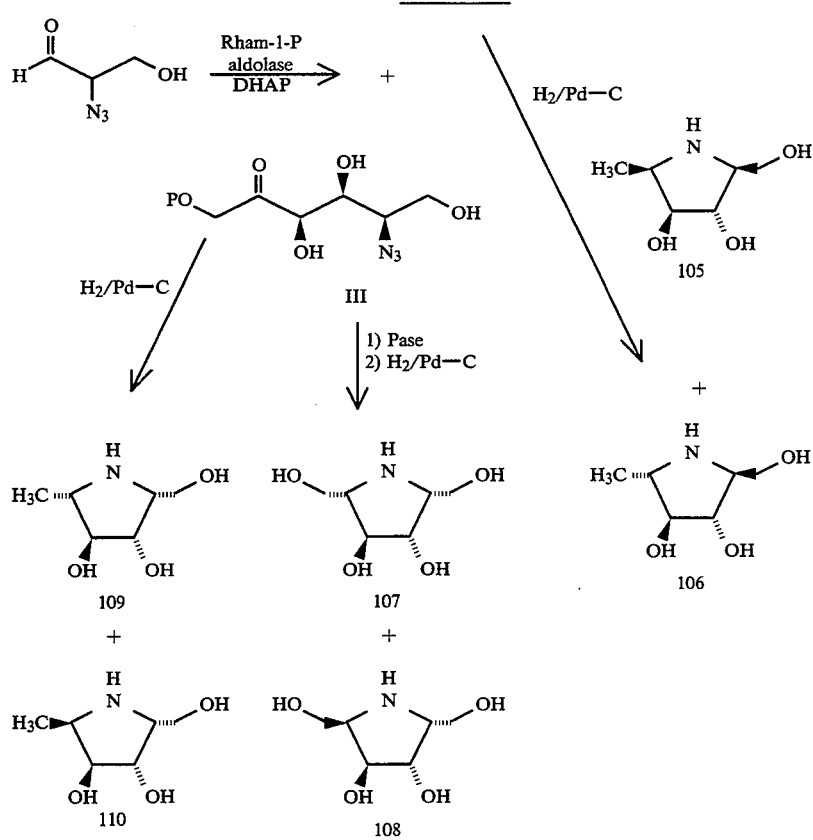

As shown below in Scheme 3a, where 2-azidopropanal is condensed with DHAP in the presence of Rham-1-P aldolase, two azido-substituted α-ketose phosphate compounds are formed: a kinetic product (Compound IIa) and a thermodynamic product (Compound IIIa). Where Compound IIa is 1) dephosphorylated and then 2) reductively cyclized by hydrogenation, diastereomeric Compounds 103a and 104a are formed.

Where Compound IIIa is directly reductively cyclized by hydrogenation, diastereomeric Compounds 105a and 106a are formed.

Where Compound IIIa is 1) dephosphorylated and then 2) reductively cyclized by hydrogenation, diastereomeric Compounds 107a and 108a are formed.

Where Compound IIIa is directly reductively cyclized by hydrogenation, diastereomeric Compounds 109a and 110a are formed.

Scheme 3a

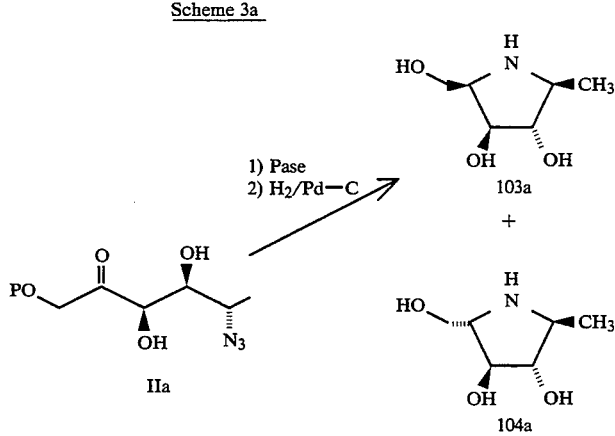

Scheme 3a

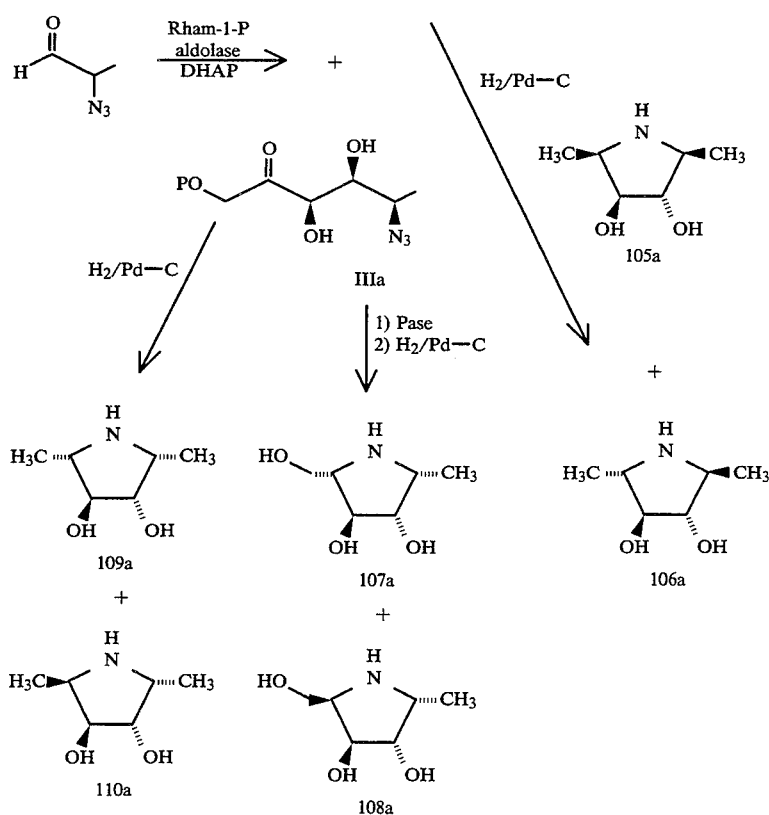

3. Fuculose-1-phosphate (Fuc-1-P) Aldolase

As shown below in Scheme 4, 2-azido-3-hydroxypropanal is condensed with DHAP in the presence of Fuc-1-P aldolase to form azido-substituted α-ketose phosphate Compound IV. Compound IV is (1) dephosphorylated and then (2) reductively cyclized by hydrogenation, to yield diastereomeric Compounds 111 and 112. Where Compound IV is directly reductively cyclized by hydrogenation, diastereomeric Compounds 113 and 114 are formed. Compounds 111 and 112 differ from Compounds 113 and 114, respectively, in the nature of the substituent group at the pyrrolidine 2-position.

In Compounds 111, 112, 113 and 114 the substituent groups at the pyrrolidine 3-, 4- and 5-positions have the 3S,4R,5S configuration.

Fuc-1-P Aldolase can be obtained from commercial sources (Sigma Chemical Co., St. Louis, Mo.) or isolated from *E. coli*.

Fuc-1-P Aldolase can also be obtained from a number of bacterial sources. By way of example, *E. coli* strain K-58 was treated with lysozyme (from egg white; 10 mg) in Tris buffer (45 mM, potassium chloride (KCl) 50 mM, pH=7.5; 20 mL) for one hour at 35° C. and the cell lysate fractionated to obtain an enzyme preparation.

Also, by way of example, *E. coli* fuculose-1-phosphate aldolase has been cloned and overexpressed, providing an alternate source for the enzyme [Ozaki et al., *J. Am. Chem. Soc.*, 1990, 112:4970].

Scheme 4

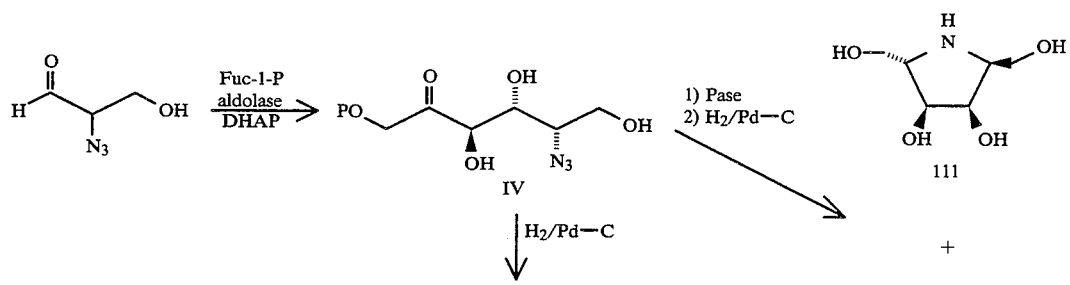

-continued

Scheme 4

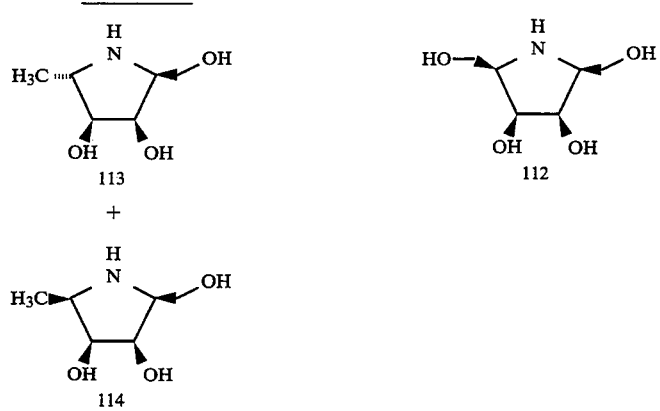

As shown below in Scheme 4a, 2-azidopropanal is condensed with DHAP in the presence of Fuc-1-P aldolase to form azido-substituted α-ketose phosphate Compound IRa. Compound IRa is 1) dephosphorylated and then 2) reductively cyclized by hydrogenation, to yield diastereomeric Compounds 111a and 112a. Where Compound IVa is directly reductively cyclized by hydrogenation, diastereomeric Compounds 113a and 114a are formed.

pound V is 1) dephosphorylated and then 2) reductively cyclized by hydrogenation, to yield diastereomeric Compounds 115 and 116. Where Compound V is directly reductively cyclized by hydrogenation, diastereomeric Compounds 117 and 118 are formed. Compounds 115 and 116 differ from Compounds 117 and 118, respectively, in the nature of the substituent group at the pyrrolidine 2-position.

In Compounds 115, 116, 117 and 118 the substituent

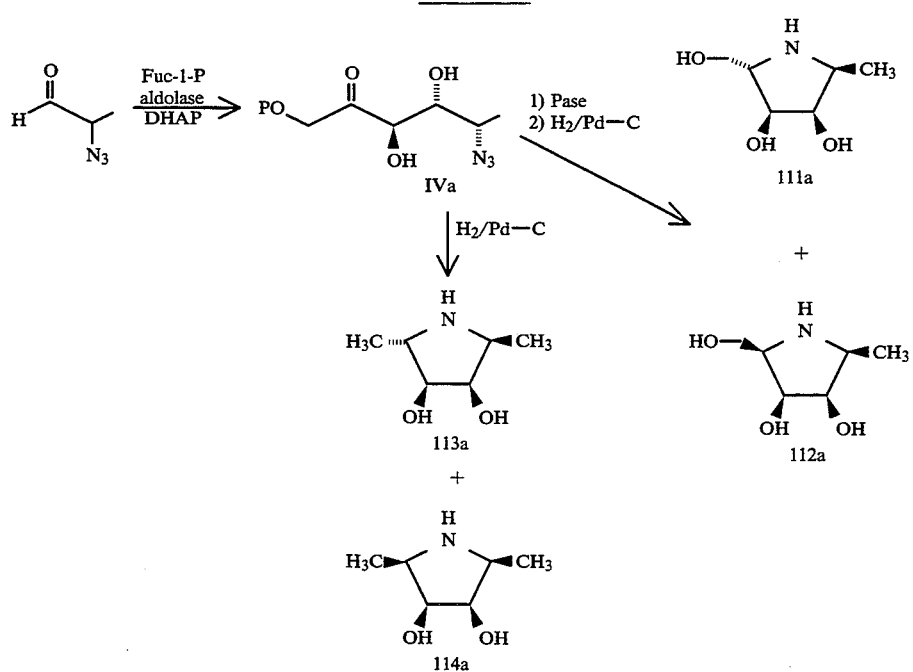

4. Tagatose-1,6-diphosphate (TDP) Aldolase

As shown below in Scheme 5, 2-azido-3-hydroxy-propanal is condensed with DHAP in the presence of tagatose-1,6-diphosphate (TDP) aldolase to form azido-substituted α-ketose phosphate Compound V. Comgroups at the pyrrolidine 3-, 4- and 5-positions have the 3R,4S,5R configuration.

TDP Aldolase can be obtained from commercial sources (Sigma Chemical Co., St. Louis, Mo.) or isolated from bacteria *Lactococcus lactis* subsp. lactis.

Scheme 5

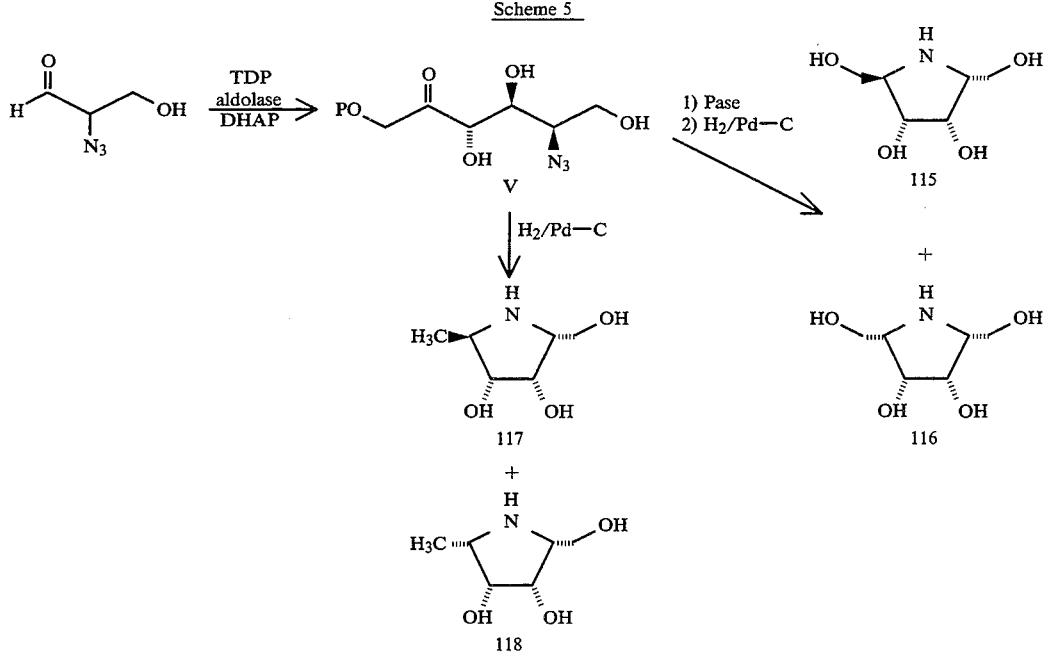

As shown below in Scheme 5a, 2-azidopropanal is condensed with DHAP in the presence of tagatose-1,6-diphosphate (TDP) aldolase to form azido-substituted α-ketose phosphate Compound Va. Compound Va is 1) dephosphorylated and then 2) reductively cyclized by hydrogenation, to yield diastereomeric Compounds 115a and 116a. Where Compound Va is directly reductively cyclized by hydrogenation, diastereomeric Compounds 117a and 118a are formed.

tion. As noted previously, the predominant least 25 percent, more preferably by about 50 percent, and most preferably by about 75 percent or more. The data hereinafter provide concentrations ($K_i$) at which 50 percent inhibition is observed in vitro for several specific glycosidases. Those $K_i$ values can be utilized as a starting concentration range for determining inhibitory concentrations in other enzymes, using standard laboratory screening procedures such as Lineweaver-Burk plots.

Scheme 5a

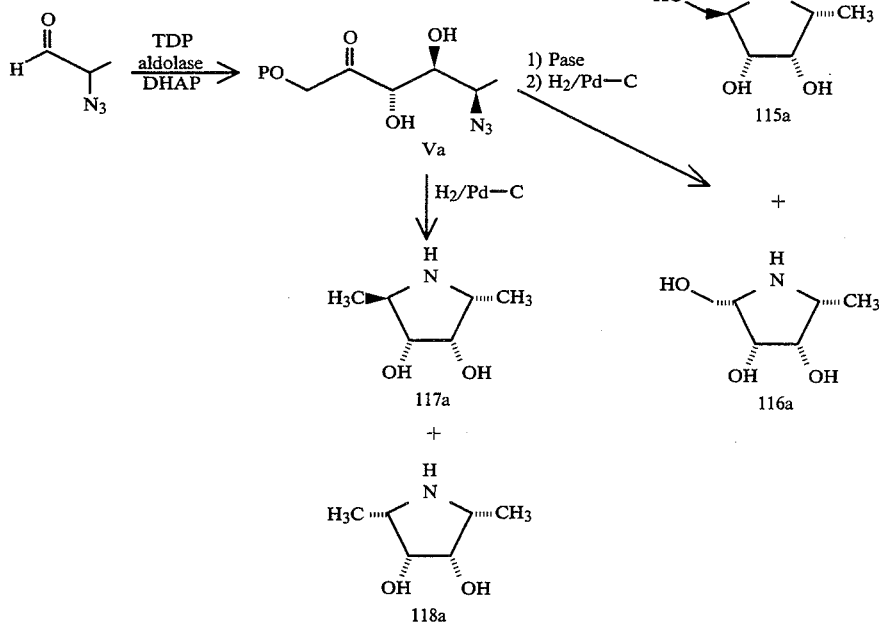

It can be seen from Schemes 2-5 and 2a-5a, above, that numerous isomers of a dihydroxypyrrolidine can be prepared by using aldolase-catalyzed asymmetric aldol condensation and reductive cyclization by hydrogena- A before-described azafuranose is dispersed in the aqueous medium. Such dispersal includes suspensions as well as true solutions in the aqueous medium. For example, a long chain alkyl or acyl group that can be present as an $R^1$ group tends to lessen water-solubility, while enhancing lipid solubility, leading to a cloudy suspension.

Results

The syntheses of (2R)-methyl-(5S)-hydroxymethyl-(3R,4R)-dihydroxypyrrolidine (Compound 1) and (2R,5S)-dihydroxymethyl-(3R,4R)-dihydroxypyrrolidine (Compound 2) are outlined below in Scheme 6. As noted earlier, an azido-substituted ketose or α-ketose phosphate can exist in solution in a straight chain or cyclic, hemiacetal form. Upon reductive cleavage of the azido group to form a primary amine that becomes the ring nitrogen atom of the azapyranose, the hemiacetal rearranges to form a cyclic imine that is further reduced to the azapyranose. Thus, Compounds 8a and 8b shown hereinafter in Scheme 6 are illustrated as hemiacetals. products obtained in Schemes 2, 3, 4 and 5 are Compounds 1, 2, 104, 106, 107, 109, 111, 113, 115, and 117.

An $R^1$ group is added to a before-described azafuranose after reductive cyclization is completed. A $C_1$–$C_{12}$ alkyl group or $C_7$–$C_{10}$ aralkyl group can be added by reductive alkylation of a corresponding aldehyde or ketone using hydrogen and a palladium on charcoal catalyst ($H_2$/Pd—C). A leaving group-substituted alkane or aralkyl compound can also be used. Exemplary leaving groups include a halide such as chloride or bromide, methanesulfonyl (mesyl) and p-toluenesulfonyl (tosyl) groups. Methods of N-alkylation are well known.

$C_1$–$C_{12}$ Acyl groups can be added via an appropriate anhydride or acid halide such as acidic anhydride or lauroyl chloride. Acylation methods are also well known.

N-Oxide derivatives are readily prepared from the N-alkyl or N-aralkyl derivatives by oxidation with hydrogen peroxide. An exemplary preparation is illustrated hereinafter.

Compositions

Also contemplated by this invention is a composition that comprises a glycosidase inhibiting amount of a before-described azafuranose (dihydroxypyrrolidine) dispersed in an aqueous medium. Preferably, the aqueous medium is a pharmaceutically acceptable medium such as normal saline, phosphate-buffered saline, Ringer's solution or the like as are well known in the art. The aqueous medium can also comprise blood, serum, plasma or lymph of a mammal such as a mouse, rat, rabbit, guinea pig, dog or human to which the azafuranose is administered.

A glycosidase-inhibiting amount is an amount that inhibits a preselected glycosidase enzyme by at

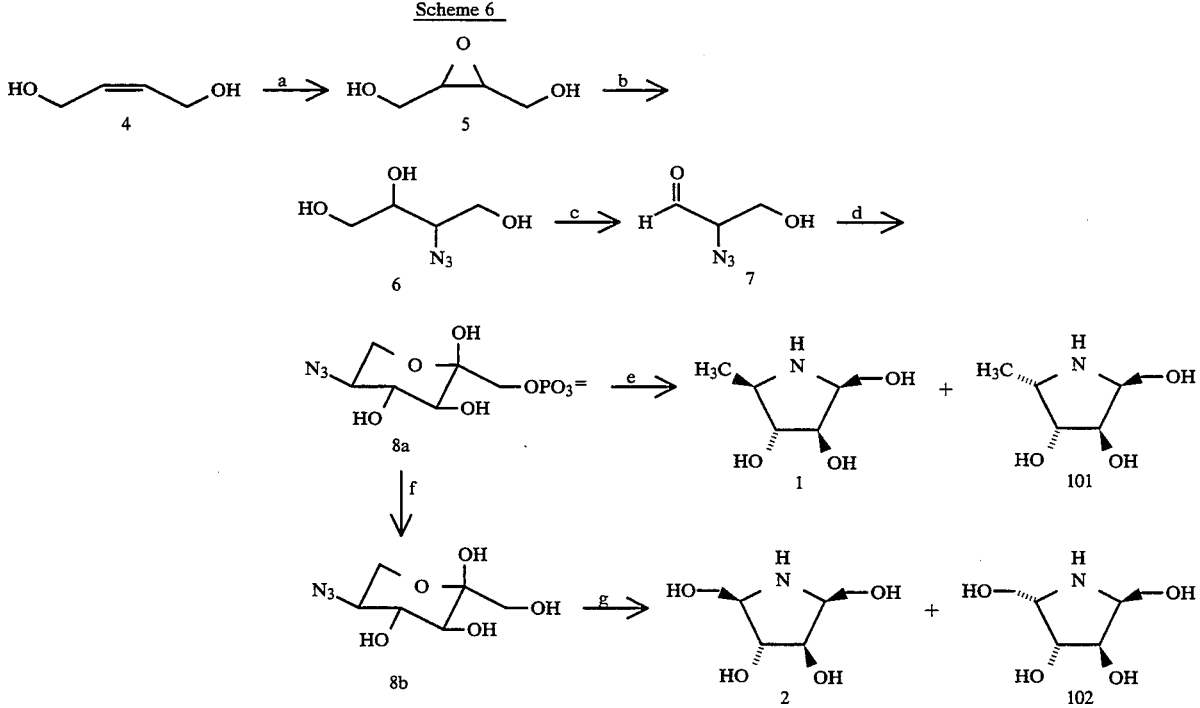

In accordance with Scheme 6, 1,4-dihydroxy-2-butene (Compound 4) was oxidized to cis-2,3-epoxy-1,4-butanediol (Compound 5) in step a. The epoxide ring of Compound 5 was nucleophilically opened in step b using sodium azide to form 2-azido-2-deoxy-threitol, Compound 6, (90 percent). Sodium periodate cleavage of compound 6 formed 2-azido-3-hydroxypropanal, Compound 7, in step c, which was not isolated.

Barium chloride was added to precipitate the formed periodite. The solution was adjusted to pH 7, then DHAP (0.5 equivalents) and FDP aldolase (from rabbit muscle, 500 Units) were added to the solution to form a reaction mixture. That reaction mixture was slowly stirred for two days to form the azido α-ketose phosphate Compound 8a. Catalytic hydrogenation of Compound 8a using Pd—C in step e, gave Compound I and its 2S-diastereomer Compound 101 in 78 percent yield, with a 2R:2S ratio of about 6:1.

It is noted that the hydrogenolysis reactions of phosphate-containing compounds are stereoselective and favor the product with a trans relation between C-2 and C-3. The reduction is proposed to proceed through an imine intermediate. The phosphate group is perhaps reductively cleaved at the imine stage to form Compound 3.

Dephosphorylation of Compound 5a with acid phosphatase produced the azido α-ketol, Compound 8b (97 percent) in step f. Palladium-catalyzed reductive cyclization provided Compound 102 and its 2R-diastereomer Compound 2 (97 percent) in step g.

Compound 2 is a particularly active glycosidase inhibitor as is seen from the data hereinafter. Compound 2 is particularly noted for its inhibitory activity being very similar to that of the known compound (2R, SR)-dihydroxymethyl-(3R,4R)-dihydroxypyrrolidine (Compound X) against α- and β-glucosidases. More surprisingly, Compound 2 exhibited significant inhibitory activity against an α-galactosidase ($K_i = 5.0 \times 10^5$M) and an α-mannosidase ($K_i = 3.1 \times 10^{-3}$M) against both of which enzymes Compound X exhibited no inhibitory activity.

The stereochemistry of the C-2 center of Compound 2 was determined to have a cis relation to H-5 based on a stronger nuclear Overhauser effect (NOE) between H-2 and H-5 than H-3 and H-5. A complete assignment of Compound 2 was established based on selective proton decoupling, NOE and coupling constants, and on the $^1$H—$^{13}$C heterocorrelation 2D spectrum.

The following examples are intended to illustrate the invention and not limit it.

EXAMPLE 1

Cis-2,3-epoxy-1,4-butane-diol (Compound 5)

Cis-2,3-epoxy-1,4-butane-diol, Compound 5, was prepared from 1,4-dihydroxy-2-butene (Compound 4) according to the reported procedure [Nelson et al., *J. Med. Chem.*, 1976, 1.9:153] except that the reaction was carried out at room temperature for 36 hours.

EXAMPLE 2

2-Azido-2-deoxy-threitol (Compound 6)

A solution containing Compound 5 (1.82 grams, 17.50 millimoles), sodium azide (NaN$_3$, 5.68 grams, 5 equivalents), and ammonium chloride (NH$_4$Cl; 4.68 grams, 5 equivalents) in 100 milliliters (mL) methanol and 12 mL H$_2$O was heated at reflux for 24 hours. The solvent was removed under reduced pressure, then ethanol was added and the precipitate was filtered off. The precipitation procedure was repeated several times to remove excess NaN$_3$ and NH$_4$Cl, to thereby obtain 2-azido-2-deoxy-threitol, Compound 6, as yellow liquid (90 percent): Rf=0.28 (EtOAc 100 percent); infrared (neat) 2109 cm$^{-1}$ (—N$_3$); $^1$H-NMR (CD$_3$COCD$_3$) δ 3.49 (1H, m) 3.59 (3H, m), 3.79 (5H, m), 4.03 (1H, t, J=5.5 Hz), 4.19 (1H, d, J=5.5), 4.30 (1H, t, J=5.5 Hz) ppm. HRMS (M+H$^+$) calculated 148. 0722, found 148. 072.

EXAMPLE 3

5-Azido-5-deoxy-L-xylo-hexulose-1-phosphate (Compound 8a)

A solution containing Compound 6 prepared above (476 milligrams, 3.24 millimoles) in 10 mL H$_2$O was cooled to zero degrees C. and sodium periodate (NaIO$_4$; 762 milligrams, 1.1 equivalent) was added. After 10 minutes, the starting material disappeared completely and a new spot appeared according to thin layer chromatography (Rf=0.5, ethyl acetate). Barium chloride (BaCl$_2$.2H$_2$O; 870 milligrams, 1,1 equivalent) was then added to the solution and the precipitate was filtered off. The solution was acidified to pH 1 with Doxew 50 (H$^+$). Racemic Compound 7, 2-azido-3-hydroxypropionaldehyde, thus prepared was not isolated.

After filtration, the solution containing Compound 7 was adjusted to pH 7 with sodium hydroxide (NaOH; 10 normal). DHAP (1.5 millimoles) was then added and the solution was readjusted to pH 7 with 10 normal NaOH. To that solution, rabbit muscle FDP aldolase (500 units) was added and the solution was stirred slowly for 2 days. Enzymatic assay indicated that all of the DHAP had been consumed.

Compound 8a was first isolated as the barium salt by adding two equivalents BaCl$_2$.2H$_2$O to the reaction mixture. The solution was maintained at $-20°$ C. overnight (about 18 hours). The precipitate was recovered, and treated with Dowex 50 (H$^+$) in distilled water to remove barium cations. After filtration, the solution was adjusted to pH 7 and lyophilized to obtain Compound 8a (75 percent). $^1$H-NMR (D$_2$O) δ 3.13 (1H, d, J=9.5 Hz, H-3), 3.14 (1H, ddd, J=9.5, 5, 11 Hz, H-5), 3.20 (1H, t, J=11 Hz, H-6a), 3.31 (1H, t, J=9.5 Hz, H-4), 3.37 (1H, dd, J=6, 11 Hz, H-6e), 3.40-3.44 (2H, m, 2×H-1) ppm. $^{13}$C-NMR (D$_2$O) δ 61.78, 63.36, 67.35, 70.95, 97.67 (d, J=9.5 Hz) ppm. HRMS (M−4H$^+$ +5 Na$^+$) calculated 395.9540, found: 395.9538.

EXAMPLE 4

(2R) -Methyl-(5S) -hydroxymethyl-(3R,4R)-dihydroxypyrollidine; (2,5,6-Trideoxy-2,5-imino-D-fructose) ( Compound 1)

A solution of Compound 8a (100 milligrams, 0.35 millimoles) in 5 mL water was hydrogenated with 20 milligrams 10 percent palladium-carbon (Pd—C) under 40 pounds per square inch (psi) of hydrogen for one day. The catalyst was removed by filtration and the filtrate was concentrated in vacuo. The residue was chromatographed on silica gel column (methanol: chloroform: H$_2$O=6:4:2) to yield Compound 1 (40 milligrams, 78 percent yield, 2R:2S≈6:1). $^1$H-NMR (D$_2$O) δ 1.31 (3H, d, J=7 Hz, 2R—CH$_3$), 1.27 (3H, d, J-6.5 Hz, 2S—CH$_3$), 3.36 (1H, m, H-2), 3.66 (1H, m, H-5), 3.74~3.81 (2H, m, 2×H-5), 3.85 (1H, m, H-3), 4.08 (1H, dd, J=2.5, 4.5 Hz, H-4) ppm; $^{13}$C-NMR (D20) δ 16.58 (C-2'), 57.90 (C-5'), 61.50, 63.44, 75.62, 87.09 ppm. HRMS (M+H$^+$) calculated 148. 0974, found 148.0974.

EXAMPLE 5

5-Azido-5-deoxy-L-xylo-hexulose Compound 8b)

Compound 8a was prepared as described before, but was not precipitated as the barium salt. Rather, after the enzymatic assay indicated that all of the DHAP had been consumed, the pH value of the solution was adjusted to 4.7 with 2N HCl. Acid phosphatase (400 U) was added and the mixture was incubated at 37° C. for 36 hours. The solution was adjusted to pH 7 and lyophilized. The residue was treated with methanol (MeOH) and filtered to remove the insoluble material, then MeOH was removed under reduced pressure. The crude product was purified by silica gel column chromatography (CHCl$_3$: MeOH=6:1) to yield 5-azido-5-deoxy-L-xylo-hexulose, Compound 8b, as the only product (240 mg, 78 percent, Rf=0.45 (CHCl$_3$: MeOH =4:1); $[\alpha]_D^{23} - 54.12$ (c 3.64, MeOH); $^1$H-NMR (D$_2$O) δ 3.32 (1H, d, J$_{1,1'}$=11.5 Hz, H-1), 3.37 (1H, d, J$_{3,4}$=9.5 Hz, H-3), 3.38 (1H, ddd, J$_{4,5}$=9.5 Hz, J$_{5,6e}$=5 Hz, J$_{5,6a}$=11 Hz, H-5), 3.45 (1H, t, J$_{6a,5}$J$_{6a,6e}$=11 Hz, H-6a), 3.52 (1H, d, J$_{1,1'}$=11.5 Hz, H-1), 3.57 (1H, t, J$_{3,4}$=J$_{4,5}$=9.5 Hz, H-4), 3.64 (1H, dd, J$_{6e,6a}$=11 Hz, $J_{6e,5}=5$ Hz, H-6e) ppm; $^{13}$C-NMR (D$_2$O) δ 69.1, 71.6, 73.3, 80.3, 82.5, 107.6 ppm. HRMS (M+H$^+$) calculated 337.9753, found 337.9778.

EXAMPLE 6

(2R,5S) -dihydroxymethyl-(3R,4R)-dihydroxypyrrolidine (Compound 2)

A solution containing Compound 8b prepared above (70 mg, 0.34 mmole) in 10 mL H$_2$O was hydrogenated with 10 mg 10 percent Pd/C under 50 psi of hydrogen for one day. The catalyst was removed by filtration and the filtrate was concentrated in vacuo to yield (2R, 5S)-dihydroxymethyl-(3R, 4R) -dihydroxypyrrolidine, Compound 2, (55 mg, 97 percent): $[α]_D^{23}$+12.75 (c 4.00, H$_2$O); $^1$H-NMR (D$_2$O) δ 2.86 (1H, q, J=5 Hz, H-5), 3.15 (1H, q, J=6 Hz, H-2), 3.49 (1H, dd, J=5 Hz, J=11.5 Hz, H-5'), 3.50 (1H, dd, J=6 Hz, J=11.5 Hz, H-2'), 3.56 (1H, dd, J=11.5 Hz, J=5 Hz, H-5'), 3.60 (1H, dd, J=11.5 Hz, J=6 Hz, H-2'), 3.69 (1H, dd, J=5 Hz, J=3 Hz, H-4), 3.93 (1H, dd, J=5 Hz, J=3 Hz, H-3) ppm. $^{13}$C-NMR (D$_2$O) δ 60.62 (C-2'), 61.59 (C-2), 62.60 (C-5'), 65.61 (C-5), 77.86 (C-3), 79.62 (C-4) ppm. HRMS (M+H$^+$) calculated 164.0923, found 164.0911.

EXAMPLE 7

N-Methyl-(2R,5S)-dihydroxymethyl-(3R,4R)-dihydroxypyrrolidine (N-methyl Compound 2)

A solution containing Compound 2 (0.32 mmol), formaldehyde (300 ml, 37 percent by weight solution) and 10 mg of 10 percent Pd—C is hydrogenated under 45 psi of hydrogen in 10 mL of MeOH/H$_2$O (1:1) solution for one day. After filtration, the solvent is removed under reduced pressure to yield N-methyl Compound 2.

EXAMPLE 8

N-Methyl-(2R,5S)-dihydroxymethyl-(3R,4R)-dihydroxypyrrolidine N-oxide (N-methyl Compound 2 N-oxide)

Hydrogen peroxide (42 mg, 50 percent by weight solution) is added to a 1 mL H$_2$O solution containing N-methyl Compound 2 (0.062 mmol) and the mixture is stirred at room temperature for three days. The solvent is removed under reduced pressure to obtain N-methyl Compound 2 N-oxide.

EXAMPLE 9

Inhibition Studies

A. Inhibition Analysis

With these dideoxyazasugars in hand, experiments were designed to determine the inhibition kinetics and the results are summarized in Table 1. All the inhibition kinetics are competitive at pH 6.5.

B. Inhibition Study

Materials: All of the buffers, substrates and enzymes noted below were purchased from Sigma and used directly. The following solutions were prepared for enzymatic assay:

1. PIPES-NaOAc buffer [0.01 molar (M) 1,4-piperazinebis(ethanesulfonic acid) (PIPES), 0.2 M sodium acetate (NaOAc) and 0.01 mM ethylenediaminetetraacetic acid (EDTA), pH 6.5]. This buffer was prepared according to the literature procedure [Dale et al., *Biochemistry*, 1985, 24:3530].
2. α-D-Glucosidase: 1.5 milligrams of solid protein (70 Units/milligram) was dissolved in 1 mL PIPES-NaOAc buffer solution and used for assay without dilution.
3. β-D-Glucosidase: The assay enzyme solution was prepared by dissolving 20 milligrams of solid protein (4.8 Units/milligram solid) in 6 mL PIPES-NaOAc buffer solution.
4. α-D-Mannosidase: 5 milligrams of solid protein were suspended in I mL of 3M ammonium sulfate [(NH$_4$)$_2$SO$_4$] and 0.1M zinc acetate (ZnOAc).
5. α-D-Galactosidase: 5 Units of α-galactosidase were dissolved in 2.2 mL PIPES-NaOAc buffer solution.
6. β-D-Galactosidase: 0.5 milligrams of solid protein (345 Units/milligram) were dissolved in 1 mL PIPES-NaOAc buffer solution.

C. General Procedure for Enzyme Assay

For each inhibitor, four or five inhibitor concentrations, ranging from zero to 3 times K$_i$ were used to determine the K$_i$ value. At each inhibitor concentration, 5 substrate concentrations were used to obtain a single Lineweaver-Burk plot. The amount of enzyme added in each assay was adjusted so that less than 10 percent of the substrate, with its lowest substrate concentration would be consumed within one minute. The assays were monitored at 400 nanometers (nm) for measuring the released p-nitrophenol group. The following illustrates the procedure in detail.

To a 1 mL disposable cuvette was added 950 microliter (μL) NaOAc-PIPES buffer solution, 20 μL inhibitor solution and 20 μL p-nitrophenol α-D-glucoside solution (25 mM in PIPES-NaOAc buffer, pH 6.5). The solution was well mixed and 20 μL β-D-glucosidase solution was added to the cuvette to start the reaction. The reaction was monitored at 400 nanometers on a Beckman DU-70 spectrophotometer for one minute and the initial hydrolysis rate was calculated. The same procedure was repeated with four other substrate concentrations. After all the initial rates were obtained, the corresponding Lineweaver-Burk plot at that inhibitor concentration was constructed.

PIPES-NaOAc buffer was used for all the enzymes except β-N-acetyl-D-glucosaminedase, for which PIPES buffer was used.

Exemplary K$_i$ data are provided in Table 1, below.

TABLE 1

| Inhibition of Glycosidases | | |
|---|---|---|
| | K$_i$ Values (M) | |
| Enzyme | Compound 2 | Compound X* |
| α-Glucosidase (brewer yeast) | 2.8 × 10$^{-6}$ | 3.3 × 10$^{-6}$ |
| β-Glucosidase (almond) | 1.9 × 10$^{-5}$ | 7.8 × 10$^{-6}$ |
| α-Galactosidase (green coffee bean) | 5.0 × 10$^{-5}$ | No inhibition |
| β-Galactosidase (E. coli) | No inhibition at 1 mM | No inhibition |
| α-Mannosidase (jack bean) | 3.1 × 10$^{-3}$ | No inhibition |
| β-Xylosidase (A. niger) | — | 2.5 × 10$^{-4}$ |

*Fleet et al., Tetrahedron Lett., 1985, 26:3127.

EXAMPLE 10

Fucosidase Inhibition Studies

Previous studies with fucosidase have implicated the involvement of two carboxylate catalytic groups in the hydrolysis of p-nitrophenyl-α-L-fucoside (fuc-pNP)

with a general acid-base mechanism. Lipshutz et al., *J. Am. Chem. Soc.*, 1982, 104:2305. Hydrolysis occurs with retention of configuration, suggesting a double displacement mechanism or a directed hydroxyl attack with a oxocarbonium ion mechanism as has been proposed for many of the other stereochemistry retaining glycosidases. See, e.g., Ho, T.-L., "Hard and Soft Acids and Bases Principles in Organic Chemistry", Academic Press, New York (1977); and Pederson et al., *Tetrahedron Lett.*, 1991, 47:2643.

Fucose is a competitive inhibitor versus fuc-pNP ($K_i$=0.30±0.01 mM) and phenol, used as an analog of p-nitrophenol, is a noncompetitive inhibitor ($K_{ii}$=112±16 mM and $K_{is}$=0.18±0.02 mM). The kinetic mechanism implicated from these studies is uni-bi sequential ordered with p-nitrophenol being released first and fucose released second.

α-L-Fucosidase activity was measured by incubating the enzyme (0.005 Units) with fuc-pNP (0.2–2.0 μM) in 0.4 ml of 50 mM acetate buffer, pH 5.5 for 20 minutes at 25° C. in the absence and presence of the azasugars of the present invention. The reaction was stopped by the addition of 0.8 ml of 2 mM glycine buffer, pH 10.5. The amount of formed p-nitrophenol was determined by optical density spectroscopy at a wavelength of 400 nm. Exemplary $K_i$ data are shown below in Table 2.

TABLE 2

| α-L-Fucosidase Inhibition | |
|---|---|
| Compound | $K_i$ (mM) |
| Mixture of 1 and 101 | 0.004 ± 0.002 |
| L-1-deoxyfuconojirimycin | 1 × 10$^{-5}$ |
| D-1-deoxyrhamnojirimycin | 0.01 ± 0.001 |
| D-1-deoxytalonojirimycin | 0.05 ± 0.006 |
| D-1-deoxymannojirimycin | 0.03 ± 0.01 |
| L-fucose | 0.30 ± 0.01 |

EXAMPLE 11

(2S)-Hydroxymethyl-(5R)-hydroxymethyl-(3S,4S)-dihydroxypyrollidine; Compound 107)

DHAP (0.5 mmole) was added to an aqueous solution of 2-azido-3-hydroxypropanal (1 mmole in 40 ml) and the pH value adjusted to 7.0 with 10N NaOH. To this solution was added rhamnulose-1-phosphate aldolase from *E. coli* (4 g), which had been treated with egg white lysozyme (40 mg) in Tris buffer (pH 7.5, 25 ml) for one hour at 35° C., to form a mixture and the mixture stirred slowly for two days. The stirred mixture was adjusted to a pH value of 4.7, and acid phosphatase (400 units) added. The resulting mixture was incubated at 37° C. for 48 hours, neutralized to a pH value of 7.0 and lyophilized. The residue was treated with MeOH and filtered to remove the insoluble material. The MeOH was removed under reduced pressure and the crude product purified with silica gel column chromatography (CHCl$_3$:MeOH=6:1) to give 5-azido-5-deoxy-D-xylo-hexulose in 30 percent yield.

Rf=0.27 (CHCl$_3$: MeOH=4:1); $[\alpha]_D^{23}$+44.12 (c 3.2, MeOH); $^1$H-NMR (CD$_3$OD) δ 3.26 (1H, ddd, J=6, 9.5, 11 Hz, H-5), 3.30 (1H, d, J=11.5 Hz, H-1), 3.33 (1H, d, J=9.5 Hz, H-3), 3.47 (1H, t, J=11 Hz, H-6a), 3.50 (1H, d, J=11 Hz, H-1), 3.50 (1H, dd, J=5, 11 Hz, H-6e), 3.58 (1H, t, J=9.5 Hz, H-4) ppm; $^{13}$C-NMR (CD$_3$OD) δ 61.33, 63.45, 65.34, 72.43, 74.84, 98.93 ppm. HRMS (M+Na$^+$+H$^+$+D$^+$) calculated 229.0659, found 229.0659.

5-Azido-5-deoxy-D-xylo-hexulose (10 mg, 0.048 mmole) prepared above was hydrogenated with 10 percent Pd/C under 45 psi of hydrogen for 1 day in 10 ml of water. The catalyst was removed by filtration and the filtrate concentrated in vacuo and further purified with a Biogel P2 column to give Compound 107 in 67 percent yield (5 mg).

$[\alpha]_D^{23}$= −24.45 (c 1 H$_2$O); R$_f$=0.65 (isopropanol:N-H$_4$OH:H$_2$O=6:3:2); $^1$H-NMR (D$_2$O) δ 3.592 (1H,m), 3.81–4.03 (5H,m), 4.08 (1H, broad s), 4.252 (1H, broad s) ppm. $^{13}$C-NMR: 57.61 (CH$_2$), 60.00 (CH$_2$), 63.90, 67.59, 75.25, 76.72 ppm. HRMS: (M+H+): calced: 164.0923, found: 164.0931.

EXAMPLE 12

Reductive Alkylation of Dihydroxypyrrolidines

About 4 equivalents of an aldehyde (formaldehyde, butanal or phenylacetaldehyde) are added to 10 ml MeOH containing about 10 mg (0.06 mmole) of a dihydroxypyrrolidine of the present invention and 10 mg of 10% Pd/C to form a mixture. The mixture is hydrogenated under 50 psi of hydrogen for 24 hours. The catalyst is filtered off and the solvent is removed under reduced pressure. The residue is purified with silica gel column chromatography to give N-alkyl derivatives of the dihydroxypyrrolidines in good yield.

The foregoing is intended as illustrative of the present invention but not limiting. Numerous variations and modifications may be effected without departing from the true spirit and scope of the novel concepts of the invention.

What is claimed is:

1. A process of making a 5-azido-5-deoxyhexulose-1-phosphate comprising mixing a 2-azido-substituted-propionaldehyde and dihydroxyacetone phosphate in the presence of a catalytic amount of an aldolase to form a reaction mixture and maintaining the reaction mixture under biological reaction conditions for a time period sufficient to form said 5-azido-5-deoxy-hexulose-1-phosphate.

2. The process according to claim 1 wherein the 2-azido-substituted-propionaldehyde is 2-azido-3-hydroxy-propanal and the formed compound is 5-azido-5-deoxy-L-xylo-hexulose-1-phosphate.

3. The process according to claim 1 wherein the 2-azido-substituted-propionaldehyde is 2-azidopropanal and the formed compound is 5-azido- 5,6-dideoxy-L-xylo-hexulose-1-phosphate.

4. The process according to claim 1 including the further step of recovering said 5-azido-5-deoxy-hexulose-1-phosphate.

5. The process according to claim 1 wherein the aldolase is selected from the group consisting of fructose-1,6-diphosphate aldolase, rhamnulose-1-phosphate aldolase, fuculose-1-phosphate aldolase and tagatose-1,6-diphosphate aldolase.

6. A process of making a 5-azido-5-deoxy-hexulose-1-phosphate comprising mixing a 2-azido-substituted-propionaldehyde and dihydroxyacetone phosphate in the presence of a catalytic amount of an aldolase that is selected from the group consisting of fructose-1,6-diphosphate aldolase, rhamnulose-1-phosphate aldolase, fuculose-1-phosphate aldolase and tagatose-1,6-diphosphate aldolase to form a reaction mixture and maintaining the reaction mixture under biological reaction conditions for a time period sufficient to form said 5-azido-5-deoxy-hexulose-1-phosphate.

* * * * *